United States Patent
Li et al.

(10) Patent No.: US 6,759,436 B2
(45) Date of Patent: Jul. 6, 2004

(54) CLEAR MICELLIZED FORMULATIONS OF β-CAROTENE AND METHOD OF TREATING LEUKOPLAKIA

(75) Inventors: Wenjie Li, Aliso Viejo, CA (US); Edward Alosio, Coto De Caza, CA (US); David A. Rutolo, Jr., Dove Canyon, CA (US); Bricini Faith (Bim) Dema-Ala, Aliso Viejo, CA (US)

(73) Assignee: Micelle Products, Inc., Lake Forest, CA (US)

( * ) Notice: Subject to any disclaimer, the term of this patent is extended or adjusted under 35 U.S.C. 154(b) by 0 days.

(21) Appl. No.: 10/061,510

(22) Filed: Feb. 1, 2002

(65) Prior Publication Data

US 2003/0149098 A1 Aug. 7, 2003

(51) Int. Cl.$^7$ .................. A61K 31/405; A61K 31/22
(52) U.S. Cl. .................. 514/725; 514/928
(58) Field of Search .................. 514/725, 928

(56) References Cited

U.S. PATENT DOCUMENTS

| | | | | |
|---|---|---|---|---|
| 4,572,915 A | * | 2/1986 | Crooks | 514/458 |
| 5,464,870 A | * | 11/1995 | Veronesi et al. | 514/617 |
| 6,251,953 B1 | * | 6/2001 | Baranowitz | 514/764 |

FOREIGN PATENT DOCUMENTS

| | | |
|---|---|---|
| WO | WO 94/21231 A | 9/1994 |
| WO | WO 95/27483 | 10/1995 |

OTHER PUBLICATIONS

Database Biosis 'Online! Biosciences Information Service, Philadelphia, Pa. US; Dec. 1999 & Archives Of Otolaryngology Head & Neck Surgery, vol. 125, No. 12, Dec. 1999, p. 1305–1310, ISSN: 0886–4470.

* cited by examiner

Primary Examiner—Zohreh Fay
Assistant Examiner—Brian Yong S. Kwon
(74) Attorney, Agent, or Firm—Gabor L. Szekeres

(57) ABSTRACT

A clear aqueous formulation for topical application in the oral cavity of humans to treat leukoplakia contains water, β-carotene, a water miscible polyol, an unsaturated fatty acid ester, and a surfactant, preferably polyethoxylated castor oil. The formulation preferably also contains a pharmaceutically acceptable anti-oxidant, preferably d-alpha-tocopherol (vitamin E), and is in the form of an oral rinse or as a gel well suited for spreading on gums or other parts of the oral cavity. The formulation is applied in a gel form on a substantially regular daily basis to areas in the oral cavity where leukoplakia lesions are present. Persistent application of the gel results in substantial diminution or total elimination of the leukoplakia lesions.

20 Claims, No Drawings

CLEAR MICELLIZED FORMULATIONS OF β-CAROTENE AND METHOD OF TREATING LEUKOPLAKIA

BACKGROUND OF THE INVENTION

1. Field of the Invention

The present invention is in the field of formulations of β-carotene, and methods of using such formulations. More particularly, the present invention relates to clear micellized formulations of β-carotene adapted for treating leukoplakia in human patients, and to the process of such treatment.

2. Brief Description of the Prior Art

β-carotene is a well known naturally occurring substance and has been used in the prior art in nutritional supplements, vitamin or vitamin related formulations, as well as in other formulations applied to the human skin. U.S. Pat. No. 4,572,915 describes clear, micellized aqueous formulations of several fat soluble vitamins, essential nutrients, herb oils and other fat soluble pharmaceutical agents, including a formulation of β-carotene. The formulations of U.S. Pat. No. 4,572,915 are to be ingested by humans as nutritional and/or vitamin supplements.

Leukoplakia is a disease characterized by formation of white or off-white colored lesions in the mouth which have the potential of developing into oral cancer. It follows that partial or total elimination of the pre-malignant leukoplakia lesions is medically desirable, and may well serve as a life-saving measure by preventing the development of potentially disfiguring or fatal oral cancer. The present invention provides a β-carotene formulation which is specifically adapted for treating leukoplakia lesions with highly favorable results.

SUMMARY OF THE INVENTION

It is an object of the present invention to provide a clear, micellized aqueous formulation of β-carotene in a gel or oral rinse form.

It is another object of the present invention to provide a method for treating leukoplakia in human patients.

The foregoing and other objects and advantages are attained by a formulation which contains water, β-carotene, a water miscible polyol, an unsaturated fatty acid ester, and a surfactant which is preferably polyethoxylated castor oil, polysorbate or polyethoxyethylene stearate. The formulation preferably also contains a pharmaceutically acceptable antioxidant, preferably d-alpha-tocopherol (vitamin E) or its pharmaceutically acceptable derivatives having vitamin E activity. The formulation may be provided as an oral rinse or as a gel well suited for spreading on gums or other parts of the oral cavity.

The method of treatment in accordance with the invention comprises applying the formulation of the invention in the gel or oral rinse form on a substantially regular daily basis to areas in the oral cavity where leukoplakia lesions are present. Persistent application of the formulation results in substantial diminution or total elimination of the leukoplakia lesions.

DETAILED DESCRIPTION OF THE INVENTION, PREFERRED EMBODIMENTS AND SPECIFIC EXAMPLES

The following specification sets forth the preferred embodiment of the present invention. The embodiments of the invention disclosed herein are the best modes contemplated by the inventors for carrying out their invention in a commercial environment, although it should be understood that various modifications can be accomplished within the parameters of the present invention.

A principal ingredient in the formulations of the present invention is β-carotene. As is known β-carotene is a naturally occurring product and is considered a precursor to vitamin A. β-carotene is available from several commercial sources, usually as a suspension in an edible or non-toxic oil. The β-carotene which is used in the formulations of the present invention is purchased from a commercial source (Roche). It is itself a formulation containing 30 percent (%) by weight of β-carotene particles suspended in vegetable oil. The particles of β-carotene in this commercial product are of 10 microns or smaller size. All percentages provided in the present description are on a weight-by-weight basis, unless stated otherwise.

Another important or principal component of the formulations of the present invention is a pharmaceutically acceptable surfactant or emulsifying agent, the preferred example of which is polyethoxylated castor oil. Polyethoxylated castor oil is also available from several commercial sources. The product utilized in the preferred embodiments of the formulations of the present invention is obtained from BASF Aktiengesellschaft, Germany under the tradename CREMOPHOR RH-40 OR CREMOPHOR EL. Polysorbates and polyoxyethylene stearates are examples for other emulsifying agents or surfactants which can be utilized in the formulations and methods of the present invention instead of polyethoxylated castor oil. These other surfactants can also be used in combination with one another and or in combination with polyethoxylated castor oil. A function of the surfactant or emulsifying agent, such as polyethoxylated castor oil of the presently preferred embodiments, is to stabilize in micelles and thereby solubilize the β-carotene. Without micellization β-carotene would be insoluble and could only be suspended as particles in the aqueous medium of the formulation.

Still another important or principal component of the formulations of the present invention is a water miscible and pharmaceutically acceptable polyol, the preferred example of which is glycerol. An example for an alternative to glycerol is diethylene glycol. The water miscible, pharmaceutically acceptable polyol acts as an emulsifying or solubilizing agent and also increases the viscosity of the formulations of the invention. The other pharmaceutically acceptable polyol, such as diethylene glycol, can be used in combination with still another acceptable polyol, or in combination with glycerol. Generally speaking, where more than one chemical compound or substance of a certain general category (such as surfactant, polyol, preservative, flavoring agent etc.) can be utilized in the present invention, then instead of a single such compound or substance a combination of substances falling within the same general category can also be used.

U.S. Pat. No. 4,572,915, already mentioned above in the introductory section of the present application for patent, describes clear aqueous formulations of fat soluble vitamins and nutritional supplements, and a certain formulation containing β-carotene. To the extent U.S. Pat. No. 4,572,915 discloses information regarding sources for, and/or alternatives of certain components which are utilized in the present invention and also in the products of U.S. Pat. No. 4,572,915, to that extent the disclosure of U.S. Pat. No. 4,572,915 is useful for the practice of the present invention and is expressly incorporated herein by reference.

A further important component of the formulations of the present invention is an ester of an unsaturated fatty acid, the preferred example of which is ethyl linoleate. The ethyl linoleate acts as a solubilizing agent.

Another component in the formulations of the present invention is d-alpha-tocopherol (vitamin E) or a pharmaceutically acceptable derivative of d-alpha-tocopherol having vitamin E activity. D-alpha-tocopherol or a derivative having vitamin E activity is not an essential component, but its inclusion is highly advantageous because it serves as a source of vitamin E and also as a natural, pharmaceutically acceptable anti-oxidant. Instead of vitamin E or its derivative, other pharmaceutically acceptable and preferably naturally occurring anti-oxidants can also be used in the formulations of the present invention. Examples for other suitable anti-oxidants are rosemary extract (a natural product), butylated hydroxyanisole (BHA), butylated hydroxytoluene (BHT), and ascorbic acid (vitamin C). Vitamin A palmitate or other pharmaceutically acceptable form of vitamin A is still another optional component of the formulation of the present invention.

Still other components or ingredients which are advantageously included in the clear micellized β-carotene formulations of the present invention are described in connection with the description of the two main preferred forms of the formulation, namely a gel adapted for oral administration to leukoplakia affected areas in the oral cavity, and a mouth wash or oral rinse, again adapted for treatment of leukoplakia in the oral cavity. The mouth wash or oral rinse of the present invention can also be utilized as a soothing rinse by persons who are not affected by leukoplakia.

Gel Formulation

Generally speaking, a gel formulation in accordance with the invention contains the following ingredients in the following percentages (weight-by-weight):

ethoxylated castor oil (or equivalent surfactant as described above) 10 to 60%;

deionized or distilled water 10 to 50%;

glycerol (or equivalent polyol, as described above) 5 to 40%;

ethyl linoleate (or equivalent unsaturated fatty acid ester) 1 to 20%;

β-carotene 30% by-weight suspension in edible oil 0.1 to 30% by weight, thus containing 0.3 to 9.0% by weight of actual β-carotene;

d-alpha-tocopherol (vitamin E) in a composition containing 1300 IU per gram (or equivalent antioxidant) 0.1 to 12% by weight, and potassium sorbate 0.1 to 0.5% by weight.

The potassium sorbate is an optional ingredient and acts as a preservative. Other pharmaceutically acceptable preservatives such as sodium benzoate or paraben can also be used instead of, or in combination with potassium sorbate. Another optional ingredient of the gel is vitamin A palmitate or other pharmaceutically acceptable form of vitamin A.

A more preferred range of the components of the gel formulation of the invention is as follows:

ethoxylated castor oil (or equivalent surfactant as described above) 20 to 40%;

deionized or distilled water 20 to 40%;

glycerol (or equivalent polyol, as described above) 10 to 30%;

ethyl linoleate (or equivalent unsaturated fatty acid ester) 1 to 15%;

β-carotene 30% by-weight suspension in edible oil 1.0 to 10.0% by weight, thus containing 0.3 to 3.0% by weight of actual β-carotene;

d-alpha-tocopherol (vitamin E) in a composition containing 1300 IU per gram (or equivalent antioxidant) 1 to 5% by weight, and optionally potassium sorbate 0.1 to 0.5% by weight.

A presently preferred exemplary embodiment of the gel of the present invention has the following composition.

ethoxylated castor oil 31%;

deionized water 30%;

glycerol 22%;

ethyl linoleate 8.5%;

β-carotene 30% by-weight suspension in edible oil 5.60% by weight, thus containing 1.68% by weight of actual β-carotene;

d-alpha-tocopherol (vitamin E) in a composition containing 1300 IU per gram 2.7% by weight, and optionally potassium sorbate 0.2% by weight.

Oral Rinse Formulation

Again generally speaking, an oral rinse formulation in accordance with the invention contains the following ingredients in the following percentages (weight-by-weight):

deionized or distilled water 50 to 95%;

glycerol (or equivalent polyol, as described above) 1 to 10%;

crystalline xylitol, or other sweetener accepted and known in the food and nutritional supplement industry, 1 to 10%;

flavoring agent, such as natural spearmint flavor, in combination of all flavors, 0.2 to 3%;

ethoxylated castor oil (or equivalent surfactant as described above) 0.01 to 5%;

sodium benzoate or other preservative 0.01 to 0.5%;

cetyl pyridinium chloride or other pharmaceutically acceptable anti-bacterial agent, 0.01 to 2%;

β-carotene 30% by-weight suspension in edible oil 0.01 to 4.0% by weight, thus containing 0.003 to 1.2% by weight of actual β-carotene;

ethyl linoleate (or equivalent unsaturated fatty acid ester) 0.01 to 2%;

disodium EDTA or other pharmaceutically acceptable chelating agent, 0.005 to 0.5%;

d-alpha-tocopherol (vitamin E) in a composition containing 1300 IU per gram (or equivalent antioxidant) 0.001 to 2.3% by weight;

vitamin A palmitate in a composition containing 1.7 mm IU per gram, or other pharmaceutically acceptable derivative of vitamin A, having vitamin a activity, 0.001 to 1.2%;

a pharmaceutically acceptable anti-foam agent 0.0005–0.1%.

Although inclusion of the flavoring agents, sweeteners and chelating agents, such as disodium EDTA, are not essential in the oral rinse formulation of the present invention, these components are advantageous because they help to provide and maintain palatability, non-turbid appearance and a reasonable shelf-life to the oral rinse of the invention. Similarly, the preservatives and antibacterials included in the oral rinse are not absolutely necessary for the oral rinse to function for its intended purposes of acting as a soothing oral rinse and/or treating or preventing development of oral lesions and leukoplakia, but are highly advantageous for providing and maintaining a reasonable shelf-life. The antibacterial agents and the vitamin A in the oral rinse formulation also provide additional benefits to the user, whether the rinse is used to treat or prevent lesions or just as a soothing oral rinse. Examples of anti-bacterial agents other than the cetyl pyridinium chloride if the preferred embodiments are benzalkonium chloride, methylbenzethonium chloride and chlorhexidine gluconate.

The anti-foam agent included in the oral rinse composition of the present invention prevents undesired foaming. Such anti-foam agents which are accepted in the pharmaceutical and food-related industry are well known in the art and are available commercially from various sources and usually contain silicone compounds. An example is the well known commercially available "Antifoam A Compound" of Dow Corning, which is itself a formulation and not a single chemical compound.

A preferred range of the components of the oral rinse is as follows:

deionized or distilled water 70 to 95%;

glycerol (or equivalent polyol, as described above) 2 to 7%;

crystalline xylitol (or other equivalent sweetener) 2 to 7%;

flavoring agent, such as natural spearmint flavor, in combination of all flavors, 0.2 to 1.5%;

ethoxylated castor oil (or equivalent surfactant as described above) 0.01 to 1%;

sodium benzoate (or other preservative) 0.01 to 0.5%;

cetyl pyridinium chloride (or other pharmaceutically acceptable anti-bacterial agent) 0.01 to 1%;

β-carotene 30% by-weight suspension in edible oil 0.01 to 2% by weight, thus containing 0.003 to 0.60 by weight of actual β-carotene;

ethyl linoleate (or equivalent unsaturated fatty acid ester) 0.01 to 0.5%;

disodium EDTA or other pharmaceutically acceptable chelating agent, 0.005 to 0.05%;

d-alpha-tocopherol (vitamin E) in a composition containing 1300 IU per gram (or equivalent antioxidant) 0.004 to 0.8% by weight;

vitamin A palmitate in a composition containing 1.7 mm IU per gram, or other pharmaceutically acceptable derivative of vitamin A, having vitamin A activity, 0.001 to 0.3%;

a pharmaceutically acceptable anti-foam agent 0.0005–0.01%.

A presently preferred exemplary embodiment of the oral rinse of the present invention has the following composition.

deionized water 88.95%;

glycerol 5.1%;

crystalline xylitol 5.0%;

natural spearmint flavor 0.50%;

natural veltol flavor 0.20%;

ethoxylated castor oil 0.090%;

sodium benzoate 0.06%;

cetyl pyridinium chloride 0.0532%;

β-carotene 30% by-weight suspension in edible oil 0.01867% by weight, thus containing 0.00560% by weight of actual β-carotene;

ethyl linoleate 0.01500%;

disodium EDTA 0.010%;

d-alpha-tocopherol in a composition containing 1300 IU per gram 0.00885% by weight;

vitamin A palmitate in a composition containing 1.7 mm IU per gram 0.0055%;

a pharmaceutically acceptable anti-foam agent 0.001%.

Additional ingredients or components such as more or different flavoring agents, sweeteners, coloring agents and additional vitamins (water or fat soluble) may become apparent to those skilled in the art for inclusion both in the gel and oral rinse formulations of the present invention, without departing from the scope and spirit of the invention and without adversely affecting the ability of the formulations to treat leukoplakia. It should also be understood in connection with the herein listed ranges of percentages of the components, that it is not contemplated within the scope of the invention to have all or most of the ingredients present in their respective maximum listed range in any given composition, as such a composition would be incapable of existence for having more than 100% of the sum of its components. Rather, it is contemplated that when one or more ingredients are in their maximum range, then the ratios of other components are in less than their maximum range, so that the sum total of all components (listed or not listed above) is 100%.

Preparation of the Gel Formulation

It is important for the β-carotene to be solubilized and dispersed in the formulations in a micellized form, because this active ingredient of the aqueous formulations of the invention is absorbed and is substantially effective only when it is micellized. Although the micelle size of β-carotene in the formulations of the present invention has not been actually measured, measurements of somewhat analogous micellized products described in U.S. Pat. No. 4,572,915 indicated that the micelles are of approximately 2 microns or smaller. As it is well appreciated by those skilled in the art, clarity of the solution or gel indicates complete micellization whereas turbidity may indicate that the β-carotene is dispersed in particles larger than 2 micron micelles. The ensuing general description discloses a process for preparing or manufacturing the gel formulation of the present invention in such a manner that the result is a clear micellized gel suitable for treating leukoplakia in the manner described below.

General Description of the Process of Preparing the Gel Formulation of the Invention:

The β-carotene in vegetable oil (30% active ingredient, obtained from Roche) is mixed with polyethoxylated castor oil and heated under agitation to approximately 160 to 180° C., and the heating and agitation is continued until a clear homogenous albeit colored solution is obtained. Then, while still being agitated the solution is cooled to approximately 130 to 135° C. while d-alpha-tocopherol, glycerol and ethyl linoleate are added. Optionally vitamin A palmitate can also be added in this step. These three or four components themselves are at room or ambient temperature before they are added, and the addition is conducted at such a rate under continuous agitation that the temperature drops to and is maintained, if necessary by heating, at approximately 85 to 90° C. Agitating in this temperature range is continued until a clear and homogeneous solution is obtained. Thereafter, water, itself heated to approximately 60° C. and optionally potassium sorbate (or other preservative) are added. The mixture is agitated and cooled to ambient temperature until it becomes clear and homogenous to provide the gel formulation of the invention. An example of a specific process is provided below.

Specific Example of the Process of Preparing the Gel Formulation of the Invention 0.585 kg of polyethoxylated castor oil (CREMOPHOR RH-40 or CREMOPHOR EL, BASF) is mixed with 0.121 kg of β-carotene (30% actual β-carotene in vegetable oil, Roche) and the mixture is heated to 160° to 180° C. and agitated until it becomes clear and homogeneous. Thereafter, the mixture is allowed to cool to 130° C. and 0.057 kg of d-alpha tocopherol composition containing 1300 IU per gram of active ingredient, 0.585 kg of glycerol USP, 0.098 kg of ethyl linoleate and 0.036 kg of vitamin A palmitate (containing 1.7 mm IU per gram, an optional but preferred ingredient) are added while the mixture is agitated and its temperature is allowed to drop to 85 to 90° C., and is maintained under agitation in this temperature range until the mixture is clear and homogeneous. Thereafter, 0.468 kg of deionized water, itself heated to approximately 60° C., is added under agitation and the mixture is stirred and cooled to ambient temperature until it is clear and homogeneous.

Preparation of the Oral Rinse Formulation

The oral rinse formulation is prepared by mixing the components under continuous agitation at ambient temperature. Advantageously, an aqueous solution of the preservative (sodium benzoate), chelating agent (disodium EDTA) and the antibacterial agent (cetyl pyridinium chloride) is first prepared, the sweetening agent (xylitol) is added, and thereafter the remaining ingredients are added, one-by-one, at ambient temperature. Care is taken that each added component is completely dissolved before the next item is added. Specific Example of the Process of Preparing the Oral Rinse Formulation of the Invention 519.51 kg of deionized water (137.6 gallons) are added to a vessel equipped with mechanical stirrer. 0.390 kg of sodium benzoate, 0.345 kg of cetyl pyridinium chloride and 0.065 kg of disodium EDTA are added while the mixture is agitated. After each item is completely dissolved 32.47 kg of crystalline xylitol is added, and after it is dissolved the following components are added one after another, each item only after the previously added item has completely dissolved. During this process the mixture is agitated, and is maintained at ambient temperature:

glycerol USP 32.47 kg;

1.948 kg of the gel prepared in the specific example of the process of making the gel (described above)

natural spearmint flavor 3.247 kg;

natural veltol flavor 1.299 kg;

antifoam A compound 0.006 kg;

and more deionized water until a total weight of 649 kg is reached (QS with deionized water to 649 kg).

Methods of Using the Formulations of the Invention

The oral rinse formulation of the present invention is best used by rinsing the mouth with approximately 10 to 15 ml of the liquid rinse for approximately one minute or longer, twice a day or more frequently, as may be recommended by dentist or physician. Besides having a pleasant soothing and anti-bacterial effect, repetitive use frequently diminishes further development of mouth irritation and is expected to forestall or minimize the development of leukoplakia.

The gel formulation of the present invention is to be applied directly to the oral lesion (leukoplakia) preferably via a cotton applicator (Q-tip). Typically a dab of the gel sufficient to substantially cover the lesion is used in a single application to a single lesion. Approximately 5 minutes after application the mouth is to be rinsed with warm tap water. The gel is to be applied twice a day to the oral lesion, or more frequently, as recommended by physician.

Clinical Results

An open label clinical trial was carried out on 11 consenting patients with extensive disease consistent with the diagnosis of oral leukoplakia. All patients presented with potentially cancerous pre-malignant lesions, which were bi-dimensionally measurable. A baseline biopsy was taken to rule out the presence of invasive cancer. At the time of enrollment, the patients were not being treated with oral beta-carotene or with retinoids.

| Characteristics | No. of Patients | Age(s) |
| --- | --- | --- |
| Males | 2 | 72 and 73 |
| Females | 9 | range 31–81 (mean 59) |

The drug used in this study was the clear, transparent micellized gel formulation of the invention, as specifically described in its preferred embodiment.

Treatment consisted in the topical application of approximately one milliliter of the gel to the oral lesion via a cotton applicator (Q-tip), Five minutes after application, the patient rinsed her/his mouth with warm tap water. Each patient was treated twice daily for three months.

Results by the end of the three-month period of treatment were as follows:

| No. of Patients | Observed Effect |
| --- | --- |
| 2 | leukoplakia disappeared completely |
| 6 | leukoplakia decreased by 75% |
| 3 | leukoplakia decreased by 50% |

In no patient did the lesion fail to decrease by less than 50%.

A gel or liquid formulation of the present invention is considered an ideal agent for the treatment of pre-malignant lesions in the oral cavity, since a topical route deposits a high concentration of the effective agent β-carotene at its site of action, while resulting only in minimal degree of systematic absorption. Moreover, the gel and liquid are an ideal vehicle for topical application in the mouth, and because the β-carotene is micellized in the invention, its absorption is greatly increased relative to a non-micellized preparation.

What is claimed is:

1. A process of treating oral leukoplakia lesions of humans in need of such treatment, the process comprising the step of applying topically to the leukoplakia lesion an effective amount of a clear aqueous formulation comprising:

water;

a water miscible pharmaceutically acceptable polyol;

a pharmaceutically acceptable unsaturated fatty acid ester;

a pharmaceutically acceptable surfactant, and

β-carotene, said β-carotene being in a micellized form within said formulation.

2. A process in accordance with claim 1 wherein the formulation additionally comprises a pharmaceutically acceptable anti-oxidant.

3. A process in accordance with claim 2 wherein the pharmaceutically acceptable anti-oxidant is d-alpha-tocopherol or a pharmaceutically acceptable derivative of d-alpha tocopherol having vitamin E activity.

4. A process in accordance with claim 1 wherein the formulation additionally comprises a compound having vitamin A activity.

5. A process in accordance with claim 1 wherein the surfactant is polyethoxylated castor oil.

6. A process in accordance with claim 1 wherein the polyol is glycerol.

7. A process in accordance with claim 1 wherein the unsaturated fatty acid ester is ethyl linoleate.

8. A process in accordance with claim 1 wherein the formulation is a gel.

9. A process in accordance with claim 8 comprising the steps of applying the gel to the leukoplakia lesion at least twice a day.

10. A process in accordance with claim 1 wherein the formulation comprises:

10 to 50% by weight water;

5 to 40% by weight of the water miscible pharmaceutically acceptable polyol;

1 to 20% by weight of the pharmaceutically acceptable unsaturated fatty acid ester;

10 to 60% by weight of the pharmaceutically acceptable surfactant, and 0.03 to 9.0% by weight of β-carotene.

11. A process in accordance with claim 10 wherein the water miscible pharmaceutically acceptable polyol is glycerol;

the pharmaceutically acceptable unsaturated fatty acid ester is ethyl linoleate, and the pharmaceutically acceptable surfactant is polyethoxylated castor oil.

12. A process in accordance with claim 1 wherein the formulation comprises:

20 to 40% by weight water;

10 to 30% by weight of the water miscible pharmaceutically acceptable polyol;

1 to 15% by weight of the pharmaceutically acceptable unsaturated fatty acid ester;

20 to 40% by weight of the pharmaceutically acceptable surfactant, and 0.3 to 3.0% by weight of β-carotene.

13. A process in accordance with claim 12 wherein the water miscible pharmaceutically acceptable polyol is glycerol;

the pharmaceutically acceptable unsaturated fatty acid ester is ethyl linoleate, and the pharmaceutically acceptable surfactant is polyethoxylated castor oil.

14. A process in accordance with claim 13 wherein the formulation additionally comprises d-alpha-tocopherol and a compound having vitamin A activity.

15. A process in accordance with claim 14 wherein the formulation is a gel.

16. A process in accordance with claim 15 comprising the steps of applying the gel to the leukoplakia lesion at least twice a day.

17. A process in accordance with claim 1 wherein the formulation comprises:

50 to 95% by weight water;

1 to 10% by weight of the water miscible pharmaceutically acceptable polyol;

0.01 to 2% by weight of the pharmaceutically acceptable unsaturated fatty acid ester;

0.01 to 5% by weight of the pharmaceutically acceptable surfactant, and 0.003 to 1.2% by weight of β-carotene, 1 to 10% by weight of a pharmaceutically acceptable sweetener;

0.01 to 2% of a pharmaceutically acceptable antibacterial agent;

d-alpha tocopherol or a pharmaceutically acceptable derivative of d-alpha tocopherol having vitamin E activity;

vitamin A palmitate or a pharmaceutically acceptable derivative of vitamin A palmitate having vitamin A activity;

a pharmaceutically acceptable chelating agent;

a pharmaceutically acceptable antifoaming agent;

a flavoring agent, and a preservative.

18. A process in accordance with claim 17 wherein the water miscible pharmaceutically acceptable polyol is glycerol;

the pharmaceutically acceptable unsaturated fatty acid ester is ethyl linoleate;

the pharmaceutically acceptable surfactant is polyethoxylated castor oil;

the pharmaceutically acceptable sweetener is xylitol;

the pharmaceutically acceptable antibacterial agent is cetyl pyridinium chloride;

the pharmaceutically acceptable chelating agent is disodium EDTA, and the preservative is sodium benzoate.

19. A process in accordance with claim 18 wherein the formulation is an oral rinse.

20. A process in accordance with claim 19 wherein the formulation comprises:

75 to 95% by weight water;

2 to 7% by weight of glycerol;

0.01 to 0.5% by weight ethyl linoleate;

0.01 to 1% by weight polyethoxylated castor oil;

0.003 to 10.6% by weight of β-carotene, 2 to 7% by weight of xylitol;

0.01 to 1% of cetyl pyridinium chloride;

0.005 to 0.05% by weight of disodium EDTA;

0.2 to 1.5% by weight of flavoring agent, and 0.01 to 0.5% by weight of sodium benzoate.

* * * * *